(12) United States Patent
Takahashi et al.

(10) Patent No.: US 10,281,704 B2
(45) Date of Patent: May 7, 2019

(54) OBSERVATION APPARATUS AND OBSERVATION METHOD TO OBSERVE A SAMPLE WITH REFLECTED LIGHT TRANSMITTED THROUGH THE SAMPLE

(71) Applicant: OLYMPUS CORPORATION, Hachioji-shi, Tokyo (JP)

(72) Inventors: Shintaro Takahashi, Tokyo (JP); Tadashi Hirata, Tokyo (JP); Yasunobu Iga, Tokyo (JP); Shinichi Takimoto, Tokyo (JP); Takashi Miyoshi, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 40 days.

(21) Appl. No.: 15/607,666

(22) Filed: May 29, 2017

(65) Prior Publication Data

US 2017/0261732 A1   Sep. 14, 2017

Related U.S. Application Data

(63) Continuation of application No. PCT/JP2016/059686, filed on Mar. 25, 2016.

(30) Foreign Application Priority Data

Mar. 31, 2015  (JP) .................. 2015-072979

(51) Int. Cl.
*G02B 21/36* (2006.01)
*G02B 21/06* (2006.01)
(Continued)

(52) U.S. Cl.
CPC .............. *G02B 21/06* (2013.01); *C12M 1/34* (2013.01); *G02B 21/084* (2013.01); *G02B 21/14* (2013.01);
(Continued)

(58) Field of Classification Search
CPC .... G02B 21/00; G02B 21/0004; G02B 21/02; G02B 21/04; G02B 21/06; G02B 21/08;
(Continued)

(56) References Cited

U.S. PATENT DOCUMENTS 5,751,475 A    5/1998  Ishiwata et al.
6,643,061 B2 * 11/2003  Osa .................. G02B 21/06
                                                           359/232
(Continued)

FOREIGN PATENT DOCUMENTS

EP        1553166 A1    7/2005
JP       57178212 A    11/1982
(Continued)

OTHER PUBLICATIONS

International Search Report (ISR) and Written Opinion dated Jun. 21, 2016 issued in International Application No. PCT/JP2016/059686.

(Continued)

*Primary Examiner* — Arnel C Lavarias
(74) *Attorney, Agent, or Firm* — Holtz, Holtz & Volek PC

(57) ABSTRACT

Provided is an observation apparatus and an observation method with which it is possible to observe imaging subjects, such as cells or the like, without labeling the imaging subjects and without causing an increase in the apparatus size. Provided is an observation apparatus including: a light-source unit that emits illumination light upward from below a sample; and an image-capturing optical system that has an objective lens that collects transmitted light, which is the illumination light emitted from the light-source unit that has passed through the sample by being reflected above the sample and that captures, below the sample, the transmitted light collected by the objective lens.

17 Claims, 9 Drawing Sheets

(51) Int. Cl.
  *C12M 1/34* (2006.01)
  *G02B 21/24* (2006.01)
  *G02B 21/08* (2006.01)
  *G02B 21/14* (2006.01)

(52) U.S. Cl.
  CPC .......... *G02B 21/24* (2013.01); *G02B 21/361* (2013.01); *G02B 21/086* (2013.01)

(58) Field of Classification Search
  CPC .. G02B 21/082; G02B 21/084; G02B 21/086; G02B 21/088; G02B 21/10; G02B 21/12; G02B 21/125; G02B 21/26; G02B 21/24; G02B 21/34; G02B 21/36; G02B 21/361
  USPC ....... 359/362, 363, 368, 369, 385, 387, 388, 359/389, 390
  See application file for complete search history.

(56) References Cited

U.S. PATENT DOCUMENTS

| | | |
|---|---|---|
| 2001/0028497 A1 | 10/2001 | Uhl |
| 2005/0105172 A1 | 5/2005 | Hasegawa et al. |
| 2006/0072190 A1 | 4/2006 | Okugawa |
| 2007/0177255 A1* | 8/2007 | Kanegasaki ........... G02B 21/34 359/368 |
| 2008/0201083 A1 | 8/2008 | Hata et al. |
| 2010/0208053 A1 | 8/2010 | Hasegawa et al. |
| 2013/0156287 A1 | 6/2013 | Houjou et al. |
| 2013/0229707 A1 | 9/2013 | Sakaguchi |
| 2015/0253561 A1 | 9/2015 | Lee et al. |
| 2015/0264235 A1 | 9/2015 | Houjou et al. |
| 2017/0355949 A1 | 12/2017 | Hirata et al. |

FOREIGN PATENT DOCUMENTS

| | | |
|---|---|---|
| JP | 02232614 A | 9/1990 |
| JP | 07261089 A | 10/1995 |
| JP | 2001166219 A | 6/2001 |
| JP | 2003021628 A | 1/2003 |
| JP | 2004318185 A | 11/2004 |
| JP | 2004361485 A | 12/2004 |
| JP | 2005010258 A | 1/2005 |
| JP | 2005326495 A | 11/2005 |
| JP | 2006174764 A | 7/2006 |
| JP | 2007264410 A | 10/2007 |
| JP | 2008092882 A | 4/2008 |
| JP | 2009217222 A | 9/2009 |
| JP | 2011008188 A | 1/2011 |
| JP | 2011141444 A | 7/2011 |
| KR | 100813915 B1 | 3/2008 |
| WO | 2006101056 A1 | 9/2006 |
| WO | 2012029817 A1 | 3/2012 |
| WO | 2013047315 A1 | 4/2013 |
| WO | 2014038871 A1 | 3/2014 |
| WO | 2014041820 A1 | 3/2014 |

OTHER PUBLICATIONS

International Search Report (ISR) and Written Opinion dated Jun. 28, 2016 issued in International Application No. PCT/JP2016/059694.
Extended European Search Report (EESR) dated Dec. 19, 2017 issued in counterpart European Application No. 16772661.1.
International Search Report dated Mar. 22, 2016 in counterpart International Application No. PCT/JP2015/085479.
Ford, et al., "Phase-gradient microscopy in thick tissue with oblique back-illumination", Nature Methods, vol. 9, 12, pp. 1195-1197, ISSN: 1548-7091.
Ra, et al., "Phase contrast DIC illumination for AFM hybrids", Ultramicroscopy, ELSEVIEr, Amsterdam, NL, vol. 104, No. 3-4, pp. 255-260, ISSN: 0304-3991.
Webb, et al., "Condenser-free contrast methods for transmitted-light microscopy: Condenser-free contrast methods", Journal of Microscopy, vol. 257, No. 1, pp. 8-22, ISSN: 0022-2720.
Extended European Search Report (EESR) dated Oct. 29, 2018 issued in European Application No. 16772663.7.

* cited by examiner

OBSERVATION APPARATUS AND OBSERVATION METHOD TO OBSERVE A SAMPLE WITH REFLECTED LIGHT TRANSMITTED THROUGH THE SAMPLE

CROSS-REFERENCE TO RELATED APPLICATIONS

This is a continuation of International Application PCT/JP2016/059686, with an international filing date of Mar. 25, 2016, which is hereby incorporated by reference herein in its entirety. This application claims the benefit of Japanese Patent Application No. 2015-072979, filed on Mar. 31, 2015, the content of which is incorporated herein by reference.

TECHNICAL FIELD

The present invention relates to an observation apparatus and an observation method.

BACKGROUND ART

In the related art, as apparatuses for imaging subjects, such as cells or the like, without labeling the imaging subjects, there are known observation apparatuses that employ the phase-contrast observation method or differential-interference observation method (for example, see Patent Literature 1).

CITATION LIST

Patent Literature

{PTL 1} Japanese Unexamined Patent Application, Publication No. Hei 7-261089

SUMMARY OF INVENTION

Technical Problem

With the observation apparatus of Patent Literature 1, it is necessary to arrange an image-capturing optical system and an illumination optical system on either side of imaging subjects.

The present invention is an observation apparatus and an observation method with which it is possible to observe imaging subjects, such as cells or the like, without labeling the imaging subjects and without causing an increase in the apparatus size.

Solution to Problem

An aspect of the present invention provides an observation apparatus including: a light-source unit that emits illumination light upward from below a sample; and an image-capturing optical system that captures, below the sample, transmitted light, which is the illumination light emitted from the light-source unit that has passed through the sample by being reflected above the sample.

In the above-described aspect, the image-capturing optical system may be provided with an objective lens that collects the transmitted light that has passed through the sample, and the light-source unit may emit the illumination light radially outward from the objective lens toward the area above the sample.

In the above-described aspect, the light-source unit may be capable of independently emitting the illumination light from different positions in radial directions of the objective lens.

In the above-described aspect, the light-source unit may be capable of simultaneously emitting the illumination light from different positions in circumferential directions of the objective lens.

In the above-described aspect, the light-source unit may be provided with a plurality of light sources that are arranged in an area surrounding the objective lens and that can independently be turned on.

In the above-described aspect, the light-source unit may be provided with a light source that is disposed below the sample and a light-blocking member that has an opening that allows, of the illumination light coming from the light source, only the illumination light at a specific radial-direction position to pass therethrough.

In the above-described aspect, the light-source unit may be provided with a diffuser panel that diffuses the illumination light.

In the above-described aspect, the sample may be accommodated in a container formed of an optically transparent material, and the illumination light may be reflected by an inner surface of a top plate of the container, which is disposed above the sample.

In the above-described aspect, the illumination light may be reflected by a reflecting member disposed above the sample.

In the above-described aspect, the sample may be immersed in a solution, and the illumination light may be reflected by a liquid surface at the top of the solution.

Another aspect of the present invention provides an observation method including: an emitting step of emitting illumination light upward from below a sample; a reflecting step of reflecting, above the sample, the illumination light emitted in the emitting step; a transmitting step of allowing the illumination light reflected in the reflecting step to pass through the sample; and an image-capturing step of capturing, below the sample, transmitted light that has passed through the sample in the transmitting step.

DESCRIPTION OF EMBODIMENT

An observation apparatus 1 according to an embodiment of the present invention will be described below with reference to the drawings.

Figure 1:
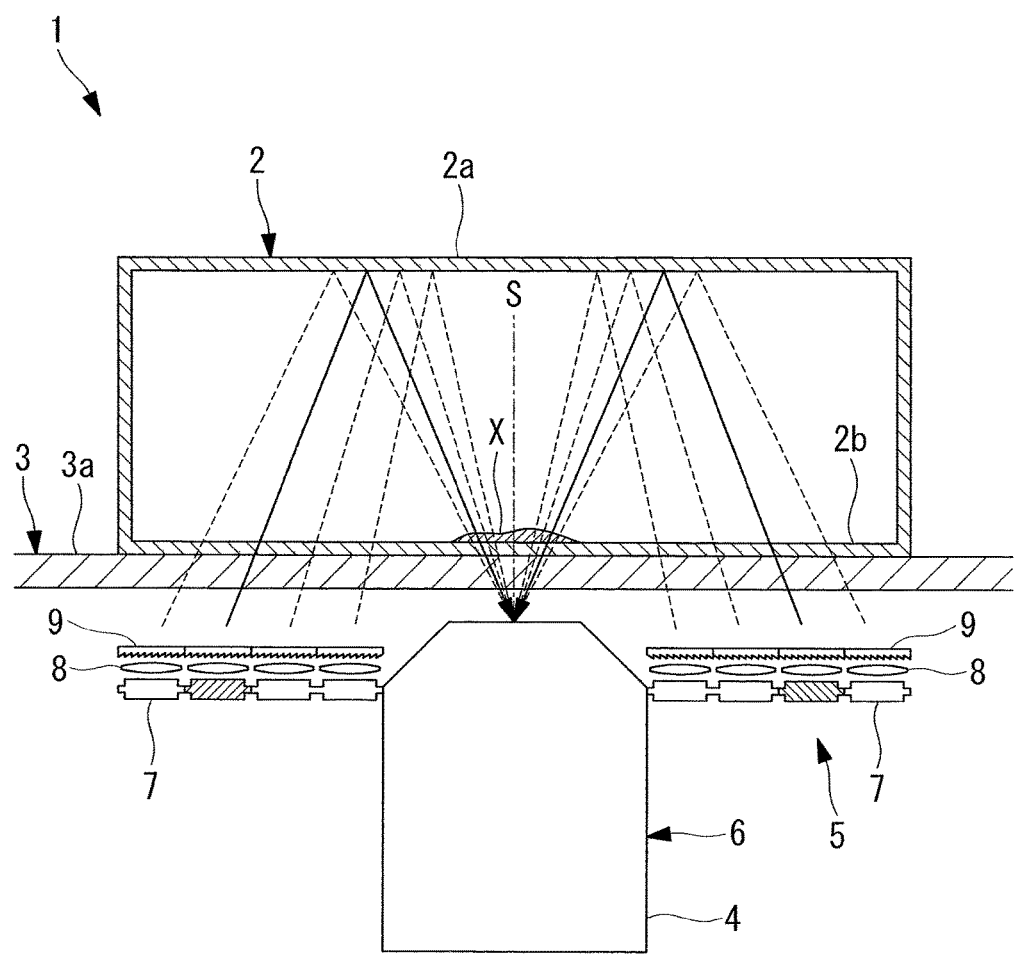
FIG. 1 is a partial longitudinal cross-sectional view showing an observation apparatus according to an embodiment of the present invention.

As shown in FIG. 1, the observation apparatus 1 according to this embodiment is provided with: a stage 3 on which a container accommodating a sample X is placed; an image-capturing optical system 6 that is disposed below the stage 3, that is provided with an objective lens 4 that collects light that has passed through the stage 3 from thereabove, and that captures the light that has passed through the sample X; and a light-source unit 5 that is disposed radially outward from the objective lens 4 and that emits illumination light that passes through the stage 3 upward.

An optically transparent material, for example, a glass plate 3a is placed on the stage 3 so as to cover the area above the objective lens 4 and the light-source unit 5, and the container 2 is configured so as to be placed on the top surface of the glass plate 3a.

The container 2 is, for example, a cell-culturing flask having a top plate 2a and is formed of an optically transparent plastic as a whole.

Figure 2:
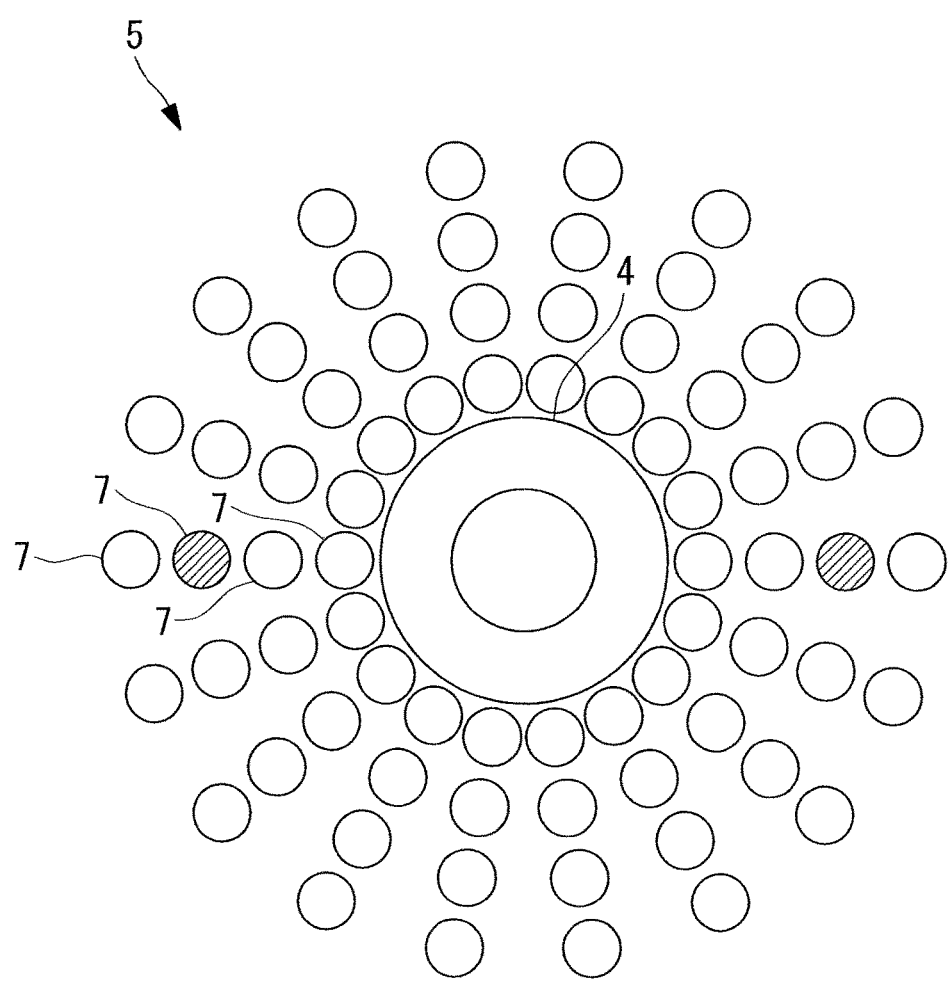
FIG. 2 is a plan view showing an example arrangement of LED light sources in a light-source unit of the observation apparatus in FIG. 1.
Figure 3:
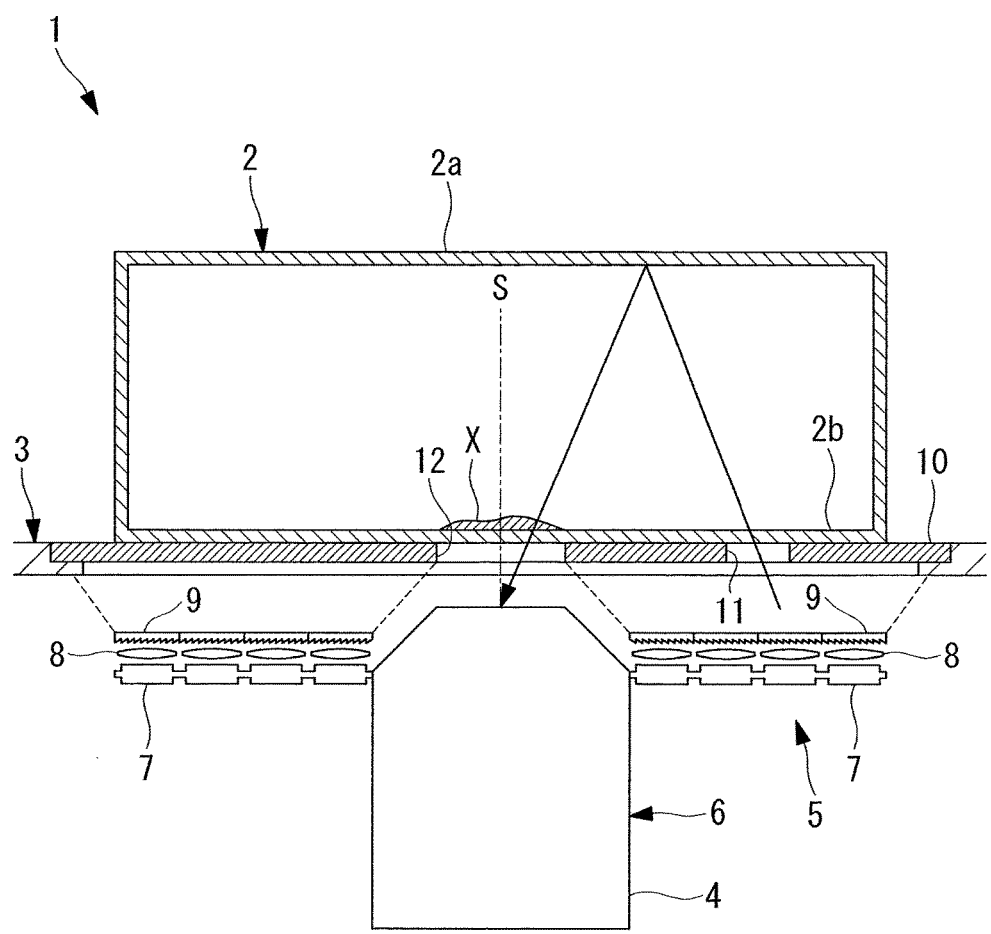
FIG. 3 is a partial longitudinal cross-sectional view of a modification of the observation apparatus in FIG. 1, showing a case in which illumination light is restricted by using a light-blocking member.

As shown in FIGS. 1 and 2, the light-source unit 5 is provided with: a plurality of LED light sources (light sources) 7 that are arranged in the area surrounding the objective lens 4 in the circumferential directions and radial directions with spaces therebetween; a plurality of focusing lenses 8 that are arranged in correspondence with the individual LED light sources 7 and that focus illumination light emitted by the individual LED light sources 7; and diffuser panels 9 that diffuse the illumination light focused by the focusing lenses 8.

The light-source unit 5 is configured so that specific LED light sources 7 can independently be turned on (the LED light sources 7 that are turned on are indicated by hatching in FIGS. 1 and 2).

In other words, by turning on only the LED light sources 7 at different positions in the radial directions of the objective lens 4, as indicated by the solid lines in FIG. 1, after passing through the glass plate 3a and a bottom surface 2b of the container 2 in the bottom-to-top direction, the illumination light is reflected by the inner surface of the top plate 2a of the container 2, thus entering the objective lens 4 by passing through, from diagonally above, the sample X, the bottom surface 2b of the container 2, and the glass plate 3a; and the angle thereof can be changed as indicated by the broken lines.

By turning on only the LED light sources 7 at specific positions in the circumferential directions of the objective lens 4, the sample X can be illuminated only from specific circumferential directions. As shown in FIG. 2, by turning on only the LED light sources 7 in two or more circumferential directions of the objective lens 4, in particular, the LED light sources 7 arranged in axi-symmetric directions with respect to an optical axis S of the objective lens 4, the sample X can be irradiated with the illumination light in which illuminance unevenness is reduced.

An observation method employing the thus-configured observation apparatus 1 according to this embodiment will be described below.

In order to observe a transparent sample X, such as cells, by using the observation apparatus 1 according to this embodiment, as shown in FIG. 1, in a state in which the sample X is accommodated in the container 2 and is adhered to the bottom surface 2b, the container 2 is placed on the glass plate 3a of the stage 3 so that the bottom surface 2b faces down.

Then, in this state, illumination light is emitted by activating some of the LED light sources 7 in the light-source unit 5. The illumination light emitted from the LED light sources 7 is focused by the focusing lenses 8 that are arranged in correspondence with the LED light sources 7, passes through the glass plate 3a and the bottom surface 2b of the container 2 in the bottom-to-top direction, after being diffused by the diffuser panels 9 (emitting step), and is reflected by the inner surface of the top plate 2a of the container 2, thus being radiated onto the sample X from diagonally thereabove (reflecting step).

Of the illumination light radiated onto the sample X, transmitted light of the illumination light that has passed through the sample X passes through the bottom surface 2b of the container 2 and the glass plate 3a in the top-to-bottom direction, and enters the objective lens 4 (transmitting step). At this time, the illumination light is refracted and scattered due to the shape and the refractive index of the sample X or is dimmed due to the transmittance of the sample X, thus being collected by the objective lens 4 in the form of transmitted light carrying information about the sample X, and is captured by an image-acquisition device (not shown) (image-capturing step).

As has been described above, with the observation apparatus 1 according to this embodiment, because the image-capturing optical system 6 that includes the light-source unit 5 and the objective lens 4 is disposed below the sample X, as compared with a conventional transmission-light observation apparatus in which the light-source unit and the image-capturing optical system are arranged on either side of a sample, there is an advantage in that it is possible to reduce the thickness of the apparatus by consolidating the light-source unit 5 and the image-capturing optical system 6 just on one side of the sample X. In the observation apparatus 1 in which the thickness thereof is reduced in this way also, there is an advantage in that, by capturing the transmitted light, it is possible to observe imaging subjects, such as cells or the like, without labeling the imaging subjects.

By being emitted radially outward from the objective lens 4 and by being reflected by the inner surface of the top plate 2a of the container 2, the illumination light coming from the light-source unit 5 is radiated onto the sample X from diagonally thereabove and is subsequently collected by the objective lens 4; therefore, there is an advantage in that, by appropriately adjusting the angle at which the illumination light enters the sample X, it is possible to form contrast in an image of the sample X, and thus, it is possible to acquire a clearly visible image even when transparent imaging subjects such as cells are used.

In this embodiment, because the light-source unit 5 is provided with the plurality of LED light sources 7 that are arranged in the radial direction in the area surrounding the objective lens 4 and that can independently be turned on, as indicated by broken lines in FIG. 1, by making the radial-direction positions of the LED light sources 7 to be turned on different, it is possible to change the irradiation angle of the illumination light that enters the sample X. By doing so, it is possible to employ bright-field illumination, which causes low illuminance unevenness, in the case in which the entry angle is smaller than the acceptance angle of the objective lens 4; additionally, it is possible to employ dark-field illumination, with which micro-structures are emphasized, in the case in which the entry angle is greater than the acceptance angle of the objective lens 4; and, furthermore, it is possible to employ oblique illumination, with which stereoscopic viewing of the sample X is possible, in the case in which the entry angle is equivalent to the acceptance angle of the objective lens 4.

In this embodiment, because the light-source unit 5 is provided with the plurality of LED light sources 7 that are arranged in the circumferential direction in the area surrounding the objective lens 4 and that can independently be turned on, by making the circumferential-direction positions of the LED light sources 7 to be turned on different, it is possible to change the irradiation direction of the illumination light that enters the sample X. By doing so, it is possible to change the direction of shadow in the formed image of the sample X, and thus, it is possible to change the appearance thereof.

As shown in FIG. 2, the illuminance unevenness is reduced by simultaneously turning on the plurality of LED light sources 7 at different circumferential-direction positions, in particular, by simultaneously turning on the plurality of LED light sources 7 disposed axi-symmetrically, and thus, there is an advantage in that it is possible to acquire an image of the sample X having low unevenness.

In this embodiment, because the diffuser panels 9 are provided in correspondence with the individual LED light sources 7, the illumination light emitted from the LED light sources 7 is uniformly diffused, and thus, it is possible to irradiate the sample X with illumination light having low illuminance unevenness and uniform intensity.

In this embodiment, the irradiation angle, the irradiation direction, and so forth of the illumination light are changed by arranging the plurality of LED light sources 7 in an arrayed manner and by independently turning on the plurality of LED light sources 7; however, alternatively, as shown in FIGS. 3 to 5B, the light-source unit 5 may be provided with the light sources 7 that are disposed in the area surrounding the objective lens 4 and a light-blocking member 10 that is disposed above the light sources 7 and that blocks the illumination light coming from the light sources 7.

Specifically, the light-blocking member 10 is provided with an opening 11 that is provided at a portion in the circumferential direction thereof or a portion in the radial direction thereof and a transmission hole 12 that allows the light that has passed through the sample X after being reflected by the inner surface of the top plate 2a of the container 2 to pass therethrough; and it is possible to change the irradiation angle and the irradiation direction of the illumination light by adjusting the position of the opening 11 by exchanging the light-blocking member 10. In this case, as with the case described above, a unit provided with the LED light sources 7 arranged in an arrayed manner, the focusing lenses 8, and the diffuser panels 9 may be employed as the light-source unit 5; however, it is permissible to employ a unit provided with an arbitrary light source so long as the light source does not require a function for changing the light-emitting position of the illumination light and so long as the light source allows the illumination light to be emitted from an area larger than that of the opening 11.

Figure 4A:
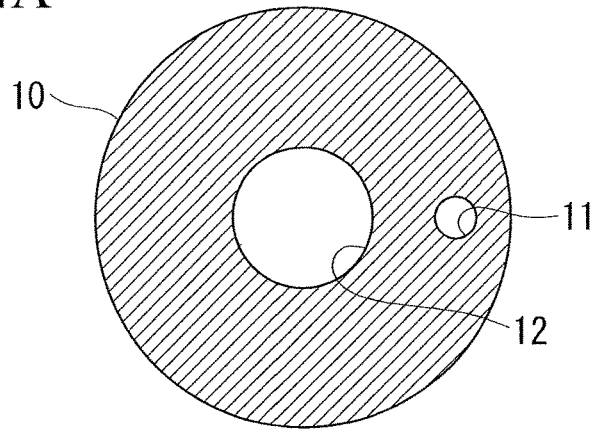
FIG. 4A is a plan view of an example of the light-blocking member in FIG. 3, showing a case in which a single circular opening is provided.
Figure 4B:
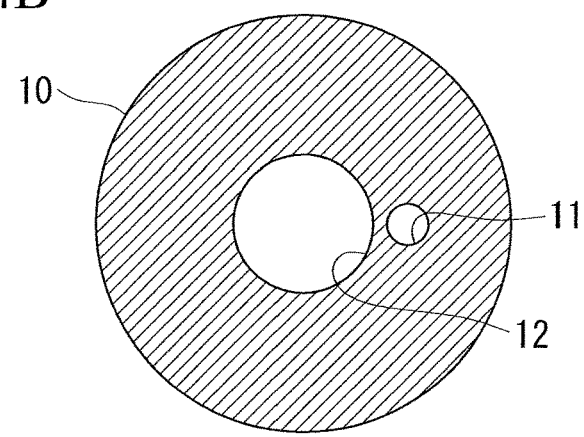
FIG. 4B is a plan view of an example of the light-blocking member in FIG. 3, showing a case in which the radial-direction position of the opening is different from that in FIG. 4A.
Figure 4C:
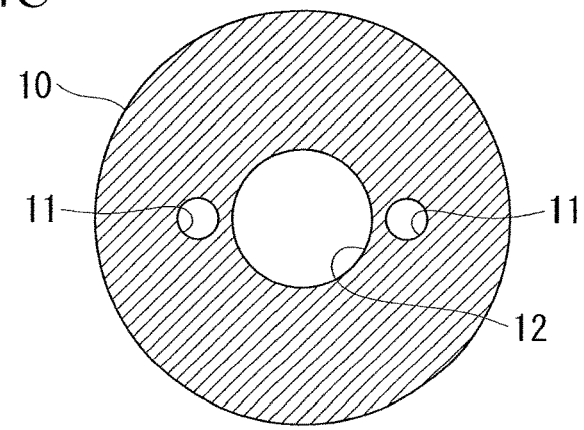
FIG. 4C is a plan view of an example of the light-blocking member in FIG. 3, showing a case in which two openings are provided.
Figure 5A:
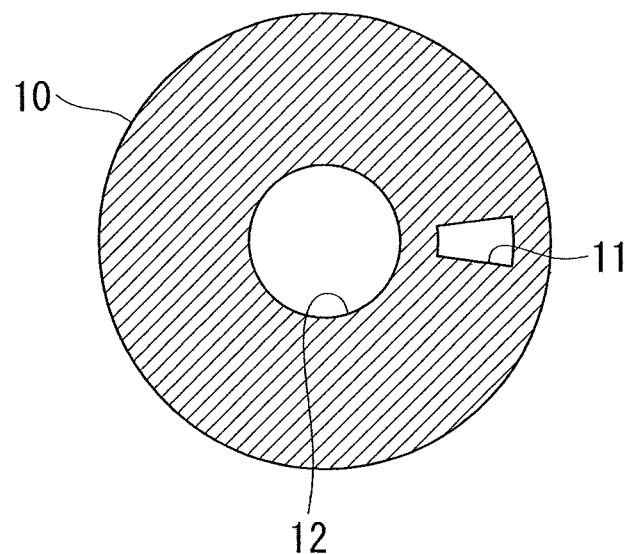
FIG. 5A is a plan view of another example of the light-blocking member in FIG. 3, showing a case in which a fan-shaped opening is provided.
Figure 5B:
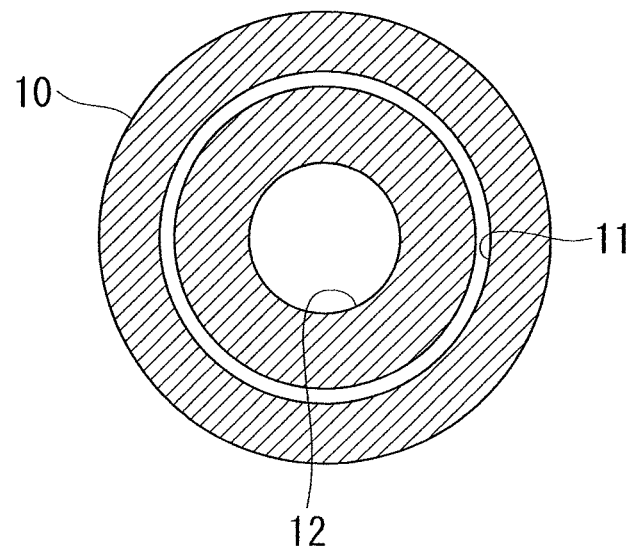
FIG. 5B is a plan view of another example of the light-blocking member in FIG. 3, showing a case in which a ring-shaped opening is provided.

FIGS. 4A to 4O show examples having circular openings 11, and examples in which radial directions thereof and the number of openings 11 differ are shown. FIG. 5A shows a case in which the opening 11 is fan shaped, and FIG. 5B shows a case in which the opening 11 is ring shaped. Arbitrary sizes, positions, and shapes can be employed for the opening 11.

Figure 6:
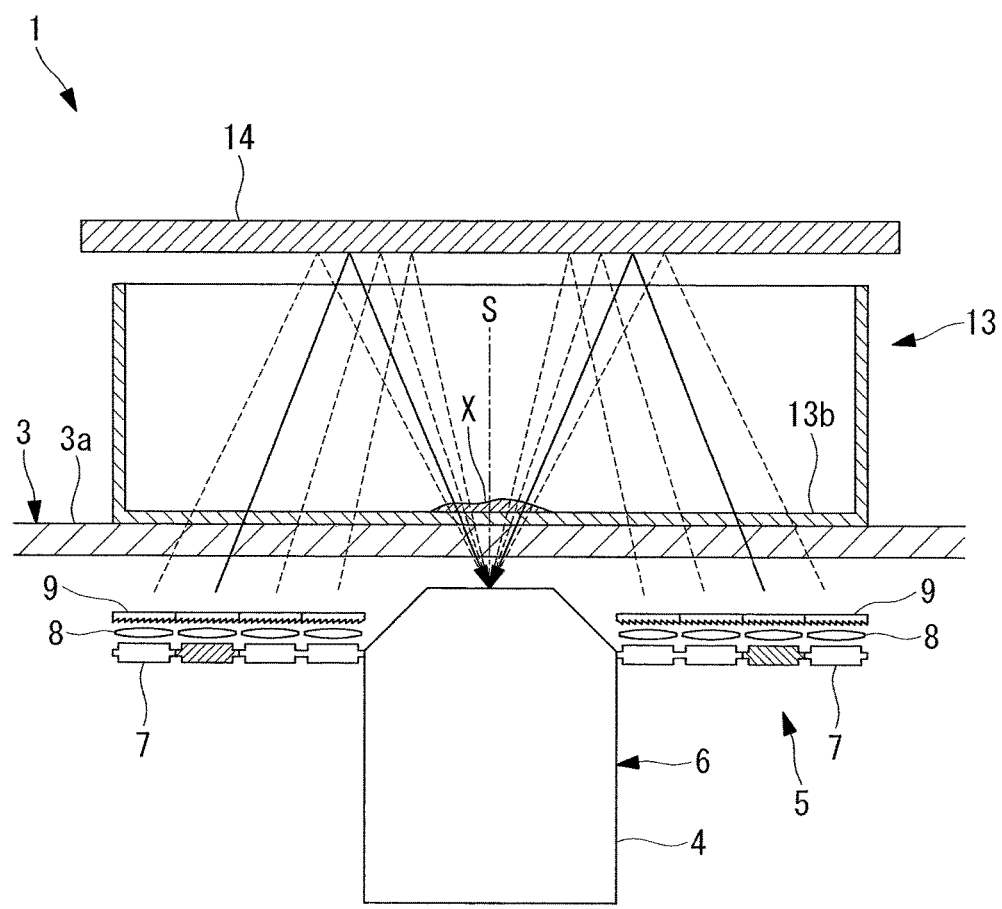
FIG. 6 is a partial longitudinal cross-sectional view showing another modification of the observation apparatus in FIG. 1.

In this embodiment, the sample X is accommodated in a container that has the top plate 2a, such as a cell-culturing flask, and the illumination light is reflected by the inner surface of the top plate 2a of the container 2; however, there is no limitation thereto. For example, with regard to the container 2, in a case in which the sample X is accommodated in a container 13 that does not have the top plate 2a, such as a petri dish (no lid), as shown in FIG. 6, a reflecting member 14, such as a mirror, may be disposed at a position that blocks the top opening of the petri dish, and the illumination light that has passed through a bottom surface 13b in the bottom-to-top direction may be reflected by the reflecting member 14. The reflecting member 14 may be provided in such a manner that it can be placed in and removed from a position above the sample X by means of a linear motion or pivoting motion.

Figure 7:
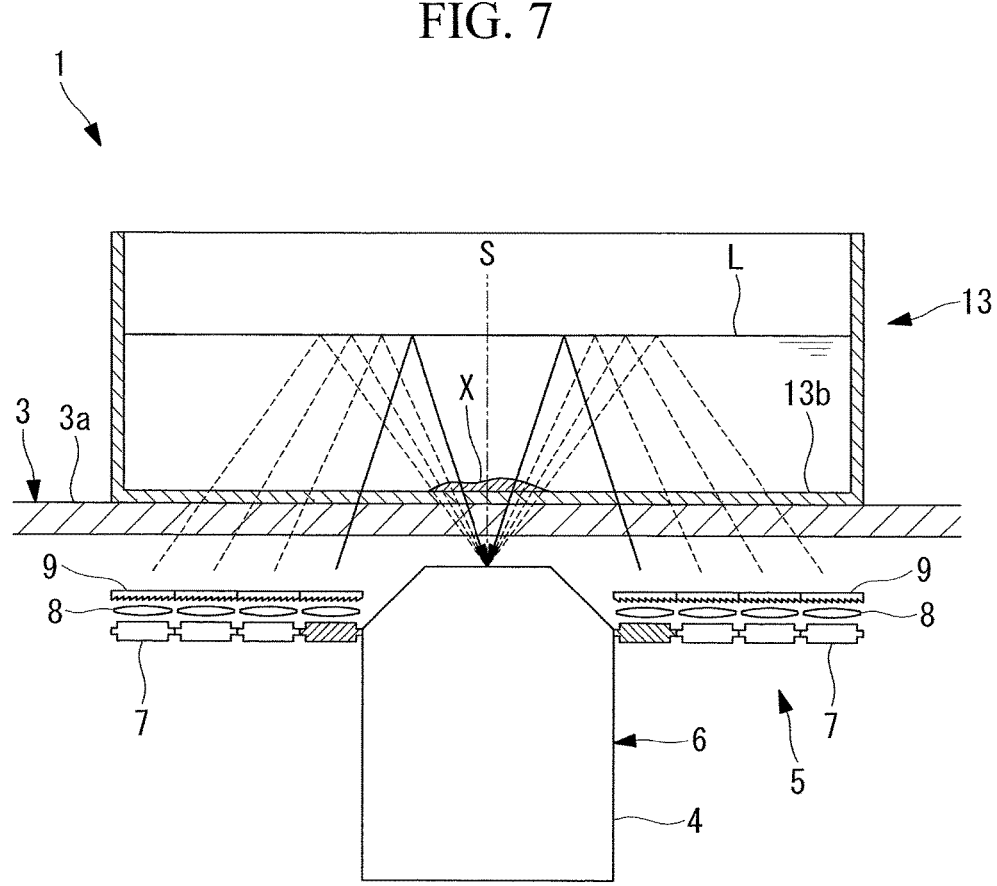
FIG. 7 is a partial longitudinal cross-sectional view showing another modification of the observation apparatus in FIG. 1.

With regard to the container 2, in the case in which the sample X is accommodated in the container 13 that does not have the top plate 2a, such as a petri dish (no lid), as shown in FIG. 7, a solution (for example, a culturing medium, a phosphate buffer solution, or the like) L may be added to the interior of the container 13, the sample X may be immersed in the solution, and the illumination light that has passed through the bottom surface 13b in the bottom-to-top direction may be reflected by a liquid surface at the top of the solution. In the case in which the sample X is accommodated in the container 2 having the top plate 2a also, the solution (for example, a culturing medium, a phosphate buffer solution, or the like) L may be added to the interior of the container 2 and the sample X may be immersed in the solution.

Figure 8:
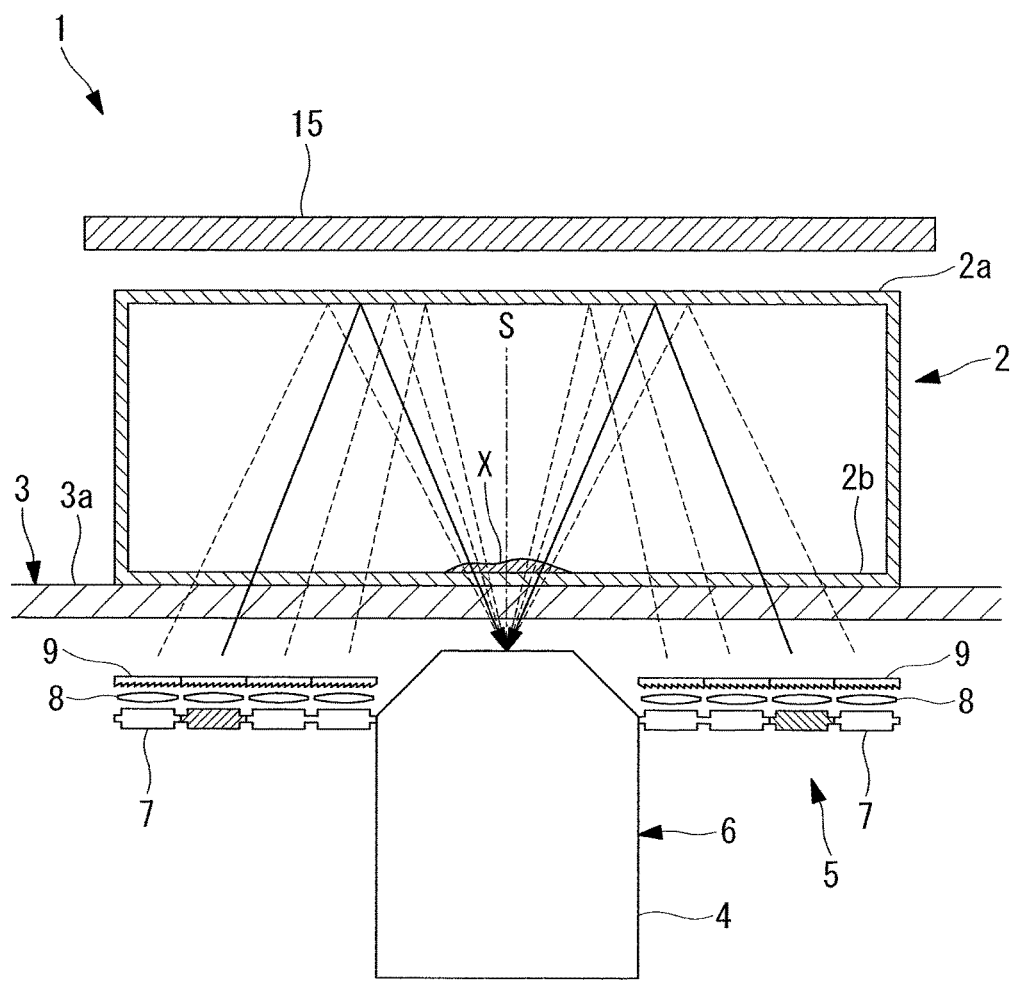
FIG. 8 is a partial longitudinal cross-sectional view showing another modification of the observation apparatus in FIG. 1.

In this embodiment, as shown in FIG. 8, a light-blocking member 15 formed of a light-blocking material may be provided above the top plate 2a.

By doing so, because external light coming from the exterior is blocked by the light-blocking member 15, it is possible to efficiently perform observation by suppressing the entry of the external light into the container 2 from the top plate 2a.

Figure 9:
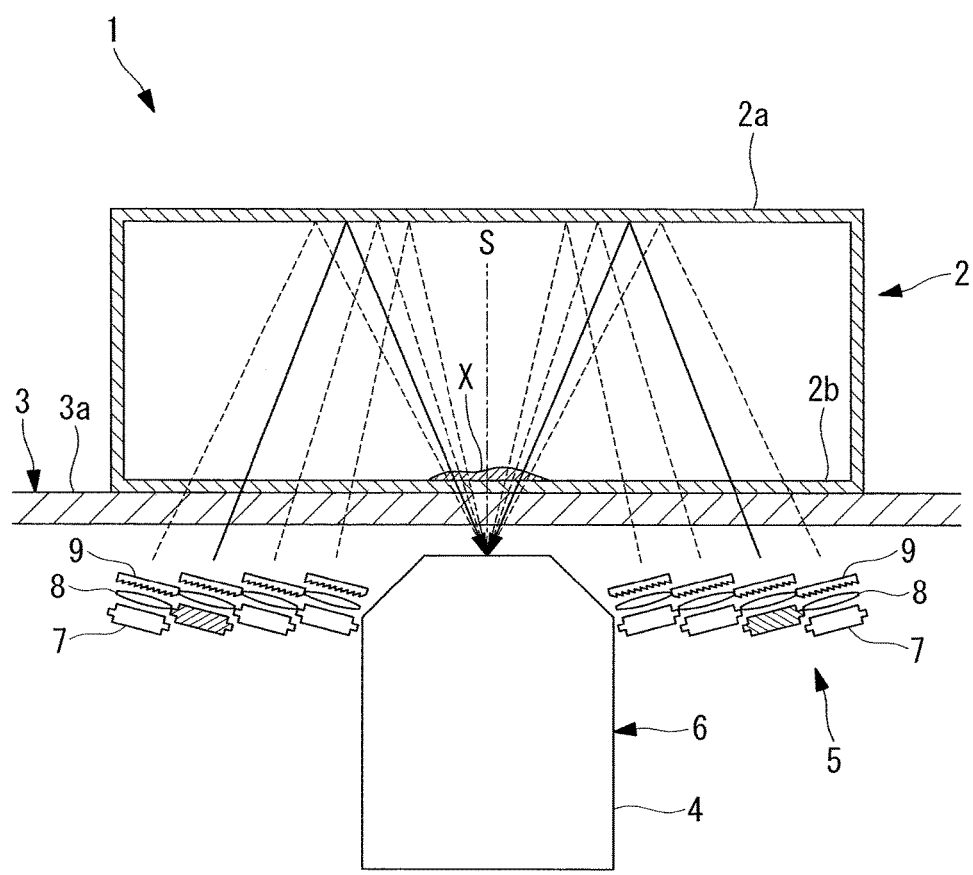
FIG. 9 is a partial longitudinal cross-sectional view showing another modification of the observation apparatus in FIG. 1.

In this embodiment, although a unit in which the LED light sources 7, the focusing lenses 8, and the diffuser panels 9 are substantially horizontally arranged so as to be parallel to the glass plate 3a has been described as an example of the light-source unit 5, alternatively, as shown in FIG. 9, the LED light sources 7, the focusing lenses 8, and the diffuser panels 9 may be disposed so as to be inclined toward the optical axis S.

By doing so, it is possible to efficiently irradiate the sample X with the illumination light by suppressing a loss of the illumination light emitted from the LED light sources 7.

Although a unit provided with the diffuser panels 9 has been described as an example of the light-source unit 5 in this embodiment, the diffuser panels 9 may be omitted.

According the above described aspect of the observation apparatus, after being emitted upward from below the sample, the illumination light emitted from the light-source unit is reflected above the sample, thus passing through the sample downward from thereabove. The transmitted light that has passed through the sample is captured by the image-capturing optical system that is disposed below the sample. Because the light-source unit and the image-capturing optical system both are disposed below the sample, it is possible, by capturing the transmitted light, to observe imaging subjects, such as cells or the like, without labeling the imaging subjects and without causing an increase in the apparatus size.

In the above-described aspect, by the image-capturing optical system is provided with an objective lens that collects the transmitted light that has passed through the sample, and the light-source unit may emit the illumination light radially outward from the objective lens toward the area above the sample, the illumination light that has been emitted, toward the area above the sample, from the light-source unit that is disposed radially outward from the objective lens disposed below the sample is reflected above the sample, and enters the sample from diagonally thereabove with respect to the optical axis of the objective lens; and the transmitted light that has passed through the sample is captured by the image-capturing optical system. By appropriately setting the angle at which the illumination light enters the sample, it is possible to form contrast in an image of the sample, and thus, it is possible to acquire a clearly visible image even when transparent imaging subjects such as cells are used.

In the above-described aspect, the light-source unit may be capable of independently emitting the illumination light from different positions in radial directions of the objective lens.

By making radial-direction positions of the illumination light emitted from the light-source unit different, it is possible to change the angle at which the reflected light reflected by the same reflecting surface disposed above the sample enters the sample. Specifically, reflected light of the illumination light emitted from a position close to the objective lens in the radial direction enters the sample at a small angle with respect to the optical axis, whereas the reflected light of the illumination light emitted from a position far from the objective lens in the radial direction enters the sample at a large angle with respect to the optical axis. By doing so, it is possible to employ bright-field illumination, which causes low illuminance unevenness, in the case in which the entry angle is smaller than the acceptance angle of the objective lens; additionally, it is possible to employ dark-field illumination, with which micro-structures are emphasized, in the case in which the entry angle is greater than the acceptance angle of the objective lens; and, furthermore, it is possible to employ oblique illumination, with which stereoscopic viewing of the sample is possible, in the case in which the entry angle is equivalent to the acceptance angle of the objective lens.

In the above-described aspect, by the light-source unit is capable of simultaneously emitting the illumination light from different positions in circumferential directions of the objective lens, the illumination light is simultaneously radiated from multiple positions in the circumferential direction of the objective lens, and thus, it is possible to reduce illuminance unevenness.

In the above-described aspect, the light-source unit may be provided with a plurality of light sources that are arranged in an area surrounding the objective lens and that can independently be turned on.

By turning on any of the plurality of light sources, it is possible to set the circumferential-direction position of the illumination light. Thus, by changing the circumferential-direction positions of the light sources to be turned on, it is possible to capture images of the sample that is illuminated from different directions. In particular, in the case of images acquired by using the above-described oblique illumination, it is possible to capture images in which shadows are formed in different ways.

In the above-described aspect, by the light-source unit is provided with a light source that is disposed below the sample and a light-blocking member that has an opening that allows, of the illumination light coming from the light source, only the illumination light at a specific radial-direction position to pass therethrough, the illumination light coming from the light sources is blocked by the light-blocking member, only the illumination light that has passed through the opening is reflected above the sample and enters the sample. Therefore, by adjusting the position of the opening in the light-blocking member, it is possible to change the direction or angle of the reflected light that enters the sample without having to change the lit positions of the light sources.

In the above-described aspect, by the light-source unit is provided with a diffuser panel that diffuses the illumination light, it is possible to irradiate the sample with the illumination light that is uniformly diffused by using the diffuser panel.

In the above-described aspect, the sample may be accommodated in a container formed of an optically transparent material, and the illumination light may be reflected by an inner surface of a top plate of the container, which is disposed above the sample.

By merely disposing the container in which the sample is accommodated and that has a top plate above the light-source unit and the image-capturing optical system, the illumination light emitted from the light-source unit can be reflected by the inner surface of the top plate of the container so as to irradiate the sample in the container.

In the above-described aspect, by the illumination light is reflected by a reflecting member disposed above the sample, in the case of observing the sample that is accommodated in a container that does not have a top plate, such as a petri dish (no lid), or a cell-culturing bag, by disposing the reflecting member above the sample, the sample in the container can be irradiated by causing the illumination light emitted from the light-source unit to be reflected by the reflecting member.

In the above-described aspect, by the sample is immersed in a solution, and the illumination light may be reflected by a liquid surface at the top of the solution, in the case of observing the sample that is accommodated in a container that does not have a top plate or a container with which the reflecting member cannot be used, the sample in the container can be irradiated by causing the illumination light emitted from the light-source unit to be reflected by the liquid surface of the solution.

REFERENCE SIGNS LIST 1 observation apparatus
2 container
2a top plate
4 objective lens 5 light-source unit
6 image-capturing optical system
7 LED light source
9 diffuser panel
10 light-blocking member
11 opening
14 reflecting member
X sample

The invention claimed is:

1. An observation apparatus comprising:
a light-source unit that is configured to be positioned at a first side of a sample, and to emit illumination light; and
an image-capturing optical system that is configured to be positioned at the first side of the sample, and to capture transmitted light, which is the illumination light that has been emitted from the light-source unit, reflected at a second side of the sample that is opposite from the first side, and passed through the sample,
wherein the image-capturing optical system comprises an objective lens that is configured to collect the transmitted light that has passed through the sample,
wherein the light-source unit is configured to emit the illumination light from a position radially outward from the objective lens, toward an area at the second side of the sample,
wherein the light-source unit is configured to emit the illumination light to the second side of the sample such that the emitted illumination light does not pass through an area of a field of view of the sample of the image-capturing optical system, and
wherein the illumination light that is reflected at the second side of the sample passes through the area of the field of view of the sample of the image-capturing optical system as the transmitted light.

2. An observation apparatus according to claim 1, wherein the light-source unit is capable of independently emitting the illumination light from different positions in radial directions of the objective lens.

3. An observation apparatus according to claim 2, wherein the light-source unit comprises a plurality of light sources that are arranged in an area surrounding the objective lens and that can independently be turned on.

4. An observation apparatus according to claim 1, wherein the light-source unit is capable of simultaneously emitting the illumination light from different positions in a circumferential direction of the objective lens.

5. An observation apparatus according to claim 1, wherein the light-source unit comprises a light source that is disposed at the first side of the sample and a light-blocking member that has an opening that allows, of the illumination light coming from the light source, only the illumination light at a specific radial-direction position to pass therethrough.

6. An observation apparatus according to claim 1, wherein the light-source unit comprises a diffuser panel that diffuses the illumination light.

7. An observation apparatus according to claim 1, wherein:
the sample is accommodated in a container formed of an optically transparent material, and
the illumination light is reflected by an inner surface of a top plate of the container, which is disposed above the sample.

8. An observation apparatus according to claim 1, wherein the illumination light is reflected by a reflecting member disposed at the second side of the sample.

9. An observation apparatus according to claim 1, wherein:
the sample is immersed in a solution, and
the illumination light is reflected by a liquid surface at a top of the solution.

10. An observation apparatus according to claim 1, wherein the light-source unit is capable of independently emitting the illumination light from different positions in a circumferential direction of the objective lens.

11. An observation apparatus according to claim 1, wherein the light-source unit is capable of changing between a first state in which the illumination light is emitted from a first position in a circumferential direction of the objective lens, and a second state in which the illumination light is emitted from a second position in a circumferential direction of the objective lens, the second position being different from the first position.

12. An observation method comprising:
emitting illumination light from a first side of a sample;
reflecting the emitted illumination light, at a second side of the sample that is opposite from the first side;
allowing the reflected illumination light to pass through the sample; and
at the second side of the sample, collecting transmitted light that has passed through the sample with an objective lens, and capturing an image of the transmitted light collected by the objective lens,
wherein the illumination light is emitted from a position radially outward from the objective lens, toward an area at the second side of the sample,
wherein the illumination light is emitted to the second side of the sample such that the emitted illumination light does not pass through an area of a field of view of the sample of the objective lens, and
wherein the illumination light that is reflected at the second side of the sample passes through the area of the field of view of the sample of the image-capturing optical system as the transmitted light.

13. An observation apparatus comprising:
a light-source unit that is configured to be positioned at a first side of a sample, and to emit illumination light; and
an image-capturing optical system that is configured to be positioned at the first side of the sample, and to capture transmitted light, which is the illumination light that has been emitted from the light-source unit, reflected at a second side of the sample that is opposite from the first side, and passed through the sample,
wherein the image-capturing optical system comprises an objective lens that is configured to collect the transmitted light that has passed through the sample,
wherein the light-source unit is configured to emit the illumination light from a position radially outward from the objective lens, toward an area at the second side of the sample, and
wherein the light-source unit is capable of independently emitting the illumination light from different positions in radial directions of the objective lens.

14. An observation apparatus according to claim 13, wherein the light-source unit comprises a plurality of light sources that are arranged in an area surrounding the objective lens and that can independently be turned on.

15. An observation apparatus comprising:
a light-source unit that is configured to be positioned at a first side of a sample, and to emit illumination light; and
an image-capturing optical system that is configured to be positioned at the first side of the sample, and to capture transmitted light, which is the illumination light that has been emitted from the light-source unit, reflected at a second side of the sample that is opposite from the first side, and passed through the sample, wherein the image-capturing optical system comprises an objective lens that is configured to collect the transmitted light that has passed through the sample, wherein the light-source unit is configured to emit the illumination light from a position radially outward from the objective lens, toward an area at the second side of the sample, and wherein the light-source unit is capable of simultaneously emitting the illumination light from different positions in a circumferential direction of the objective lens.

16. An observation apparatus comprising:

a light-source unit that is configured to be positioned at a first side of a sample, and to emit illumination light; and an image-capturing optical system that is configured to be positioned at the first side of the sample, and to capture transmitted light, which is the illumination light that has been emitted from the light-source unit, reflected at a second side of the sample that is opposite from the first side, and passed through the sample, wherein the image-capturing optical system comprises an objective lens that is configured to collect the transmitted light that has passed through the sample, wherein the light-source unit is configured to emit the illumination light from a position radially outward from the objective lens, toward an area at the second side of the sample, and wherein the light-source unit comprises a light source that is disposed at the first side of the sample and a light-blocking member that has an opening that allows, of the illumination light coming from the light source, only the illumination light at a specific radial-direction position to pass therethrough.

17. An observation apparatus comprising:

a light-source unit that is configured to emit illumination light upward from below a sample; and an image-capturing optical system that is configured to capture transmitted light below the sample, wherein the transmitted light is the illumination light that has been emitted from the light-source unit, reflected above the sample, and passed through the sample, wherein:

the sample is immersed in a solution, and the illumination light is reflected by a liquid surface at a top of the solution.

* * * * *